US00PP25060P3

(12) United States Plant Patent
Korlipara

(10) Patent No.: US PP25,060 P3
(45) Date of Patent: Nov. 11, 2014

(54) *ECHINACEA* PLANT NAMED 'METEOR RED'

(50) Latin Name: ***Echinacea* hybrid**
Varietal Denomination: Meteor Red

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 124 days.

(21) Appl. No.: 13/815,537

(22) Filed: Mar. 8, 2013

(65) Prior Publication Data

US 2014/0259245 P1 Sep. 11, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Meteor Red' characterized by enlarged disc florets forming an anemone-type inflorescence, red orange ray florets and dark red orange disc florets, ray florets which are held horizontally when young but vertically when mature, a mounding habit with excellent stem count, and excellent vigor.

1 Drawing Sheet

Botanical denomination: *Echinacea* hybrid.
Variety designation: 'Meteor Red'.

BACKGROUND OF THE INVENTION

The present invention relates to a new and distinct cultivar of *Echinacea* and given the cultivar name 'Meteor Red'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Secret Love' (U.S. Plant Pat. No. 24,504), the new cultivar has taller cones, a larger habit, larger leaves, and duller red flowers.

Compared to *Echinacea* 'Hot Papaya' (U.S. Plant Pat. No. 21,022), the new cultivar has smaller inflorescences and more crowns.

This new *Echinacea* cultivar is distinguished by:

1. enlarged disc florets forming an anemone-type inflorescence,
2. red orange ray florets and dark red orange disc florets,
3. ray florets which are held horizontally when young but vertically when mature,
4. a mounding habit with excellent stem count, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old plant of *Echinacea* 'Meteor Red' growing in the trial bed in full sun in early July in Canby, Oreg. A black background was used.

FIG. 2 shows a view looking down on a nine-month-old plant in the trial field.

DETAILED PLANT DESCRIPTION

The following is a detailed description of the new *Echinacea* cultivar based on observations of three-year-old specimens growing in the trial beds in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to about 80 cm wide and 95 cm tall to top of inflorescences.
*Form.*—Basal clump, with about 80 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 5 inflorescences per stem.
*Size.*—To 72 cm tall to a terminal inflorescence and 9 mm wide at base.

*Internode length.*—3 cm to 7 cm.
*Surface texture.*—Strigose.
*Color.*—Closest to Yellow Green 151 A tinted Greyed Purple 187A.

Leaf (basal):
*Type.*—Simple.
*Shape.*—Ovate to lanceolate.
*Arrangement.*—Basal.
*Blade size.*—Grows to 10 cm long and 6 cm wide.
*Margins.*—Coarsely serrate.
*Apex.*—Acute.
*Base.*—Attenuate.
*Surface texture.*—Strigose on both sides.
*Venation.*—Pinnate, with 3 main veins from the base, Yellow Green 145D on both sides.
*Color.*—Topside, Green 137B, bottom side closest to Yellow Green 147B.
*Petiole description.*—Grows to 14 cm long and 3 mm wide above the clasp, sparsely strigose, Yellow Green 145B.

Leaf (stem):
*Type.*—Simple.
*Shape.*—Lanceolate.
*Arrangement.*—Alternate.
*Blade size.*—Grows to 17.5 cm long and 5.5 cm wide.
*Margins.*—Coarsely serrate.
*Apex.*—Acuminate.
*Base.*—Attenuate.
*Surface texture.*—Strigose on both sides.
*Venation.*—Pinnate, with 3 main veins from the base, Yellow Green 147C on both sides.
*Color.*—Topside Green N137A, bottom side closest to Green 137C.
*Petiole description.*—On all but upper leaves, clasping, grows to 9.5 cm long and 4 mm wide above the clasp, strigose, both sides Yellow Green 147C.

Inflorescence:
*Type.*—Composite on terminal stalked heads.
*Number of flowering stems from the ground.*—About 80.
*Flowering stem.*—Grows to 72 cm tall from the base of the plant to the terminal inflorescence and can grow to 17 cm long from the top stem leaf to the base of an inflorescence; branched with 1 to 5 inflorescences per stem; diameter growing to 1 cm wide near the inflorescence; strigose; closest to Yellow Green 151A tinted Greyed Purple 187A.
*Size.*—Grows to 7.5 cm wide and 7.5 cm deep as disc enlarges.
*Form.*—Ray florets held reflexed, mature disc is conic.
*Immature inflorescence.*—Grows to 4.5 cm wide and 1.5 cm deep, ray florets held at a 10 degree angle from the horizontal and rolled up so only the back color shows, Red Purple 58A, disc color Red Purple 59A.
*Ray florets.*—Without pistil or stamen, about 28 in number, grow to 37 mm long and 7 mm wide, oblanceolate with the tip two-toothed, tips acute, entire margins, base attenuate, glabrous on both sides; top side Greyed Orange 168B when first fully open becoming tinted with Red Purple 58A when disc florets are fully open, bottom side Red Purple 58A.
*Disc.*—Flat becoming conic, growing to 45 mm deep and 57 mm wide with maturity, Red Purple 58A when disc florets are closed to Red 53B when disc florets are newly open.
*Disc florets.*—To about 400 in number, each with 1 pistil and 4 stamen, grow to 22 mm long and 10 mm wide, each with one persistent, very stiff linear bract (12 mm long with Greyed Purple 187A at apex blending to 2 mm Red Purple 59C to 5 mm Yellow Green 145D to White 155A at base); corollas to 17 mm long and 10 mm wide, tubular at base (to 3 mm long and 2 mm wide, Grey Brown 199C) then oblanceolate and fan-like with tip 2 to 5 lobed (1 side lobe linear, cut to the tube, to 9 mm long and 1 mm wide); main fan usually 12 mm long and 5.5 mm wide with 3 lobes at apex, each usually 3 mm long and 1 mm wide, margin entire, tips acute, base attenuate, glabrous on both sides, topside Red 46A when first open lightening to 47A, bottom side Greyed Orange 173A; pistil 7 mm long, ovary 4 mm long, White 155A, style 5 mm long, White 155A on bottom half and Greyed Orange 173A on top half, 2-branched stigma spreading, Greyed Orange 173A; stamen 4 mm long, filaments 2 mm long, threadlike, White 155A, anthers 2 mm long, Greyed Orange 177A, pollen Yellow 18A.
*Phyllaries.*—In 4 leafy series, area grows to 27 mm wide and 7 mm deep, lobes lanceolate in shape, reflexed, grow to 6 mm long and 2.5 mm wide, both sides Yellow Green 147B, margins strigose, tip acute, strigose.
*Receptacle.*—Grows to 19 mm wide and 22 mm deep, White 155B.
*Bloom period.*—July through October in Canby, Oreg.
*Fragrance.*—Slight.
*Lastingness.*—Each inflorescence lasts about two weeks in Canby, Oreg.
*Seeds.*—None seen.
*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

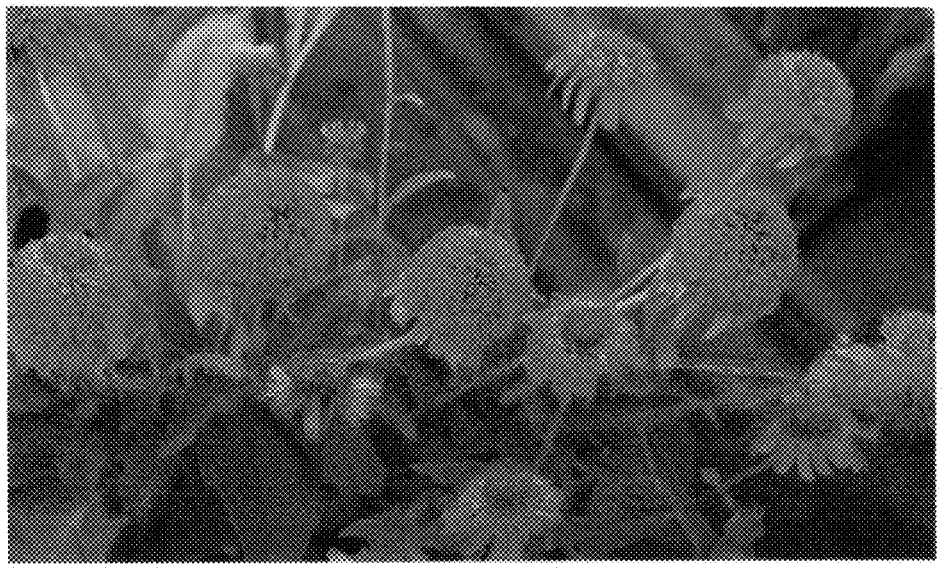

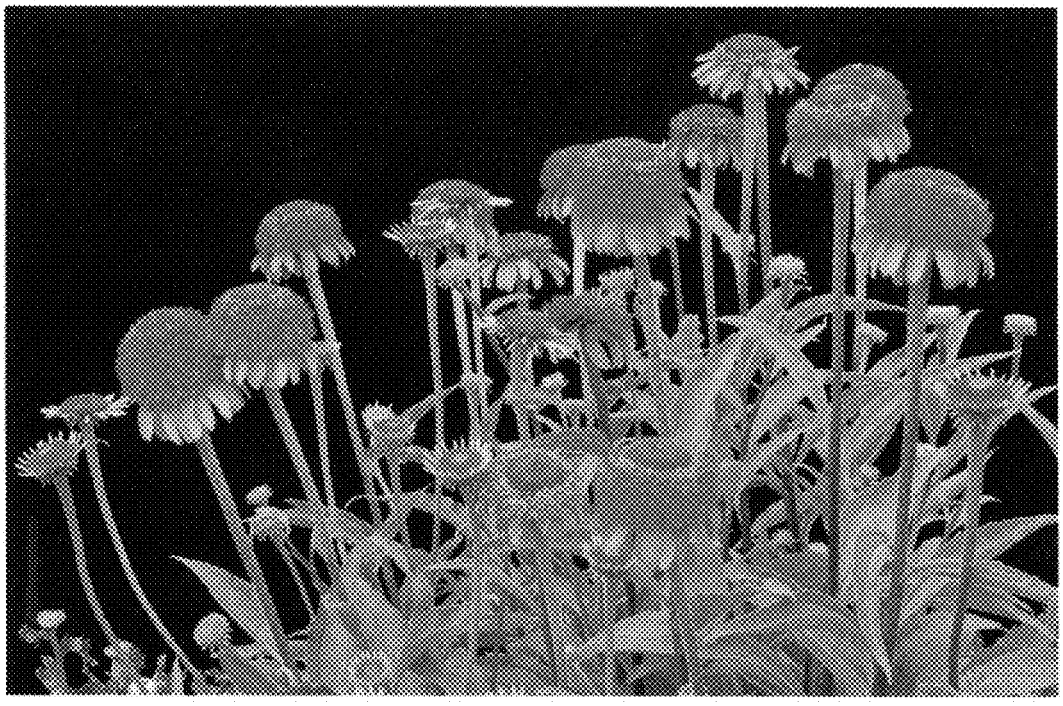
FIG. 1 above, FIG. 2 below